(12) United States Patent
Banks et al.

(10) Patent No.: US 6,635,760 B2
(45) Date of Patent: Oct. 21, 2003

(54) RING FLUORINATION OF NON-ACTIVATED AROMATIC COMPOUNDS

(75) Inventors: Ronald Eric. Banks, Stockport (GB); Mohamed Khalifa Besheesh, High Peak (GB)

(73) Assignee: Air Products and Chemicals, Inc., Allentown, PA (US)

(*) Notice: Subject to any disclaimer, the term of this patent is extended or adjusted under 35 U.S.C. 154(b) by 0 days.

(21) Appl. No.: 10/044,082

(22) Filed: Oct. 23, 2001

(65) Prior Publication Data

US 2002/0055662 A1 May 9, 2002

(30) Foreign Application Priority Data

Oct. 24, 2000 (GB) .............................................. 0026011

(51) Int. Cl.⁷ .................... C07D 251/24; C07D 251/28; C07D 253/04; C07D 253/06
(52) U.S. Cl. ...................... 544/180; 544/182; 544/215; 544/216; 544/217; 544/218; 544/219
(58) Field of Search ................................ 544/180, 182, 544/215, 216, 217, 218, 219

(56) References Cited

U.S. PATENT DOCUMENTS

4,828,764 A    5/1989    DesMarteau ................. 260/397

FOREIGN PATENT DOCUMENTS

EP    0204535    12/1986
FR    1201782    1/1960

OTHER PUBLICATIONS

Lal et al., Chem. Rev. 96, 1737–1755, 1996.*
Furin, G. G.: Methods of Organic Chemistry (Houen–Wey): vol. E10a; Organofluorine Compounds (ed. B. Baasner, et al.), Georg Thieme Verlag, Stuttgart, 1999, pp. 432–499.
Banks, R.E.: Selectfluor™ reagent F–Teda–BF₄ in action: tamed fluorine at your service. Journal of Fluorine Chemistry 87 (1998) 1–17.
Broschag, Matthias, et al.: "Synthesis and characterization of novel halogeno(+l) adduct complexes containing malononitrile and 1,3,5–triazine." Inorganica Chimica Acta, (1993), 205(2), 167–73, XP001052954.

Schleyer, Paul V. R. et al.: "Preparation of 1–Fluoro–2,4, 6–trihalogeno–s–triazinium Hexafluoroarsenates: Structure of 'C₃N₃Cl₃F!'AsF₆! As Deduced by Experimental and ab Initio Methods." Inorg. Chem. (1993), 32(8), 1523–4, XP001041857.

Schulz, A., et al.: Das Perfluortiazinium–Kation als Oxidationsmittel in der metallorganischen Synthese—Ein neuer Weg zur Darstellung von (Cp₂Mcl₂)²⁺(M=Mo,W). Journal of Organometallic Chemistry, 480 (1994) 195–197.

Broschag, M. et al.: "Fluorination of cyanuric chloride and low–temperature crystal structure of '(ClCN)₃F!+'AsF₆!–." Z. Anorg. Allg. Chem. (1994), 620(6), 1132–6, XP001052965.

Banks, R.E., et al.: N–Halogeno compounds. Part 18. 1–Alkyl–4–fluoro–1,4–diazoniabicyclo[2.2.2]octane salts: user–friendly site–selective electrophilic fluorinating agents of the N–fluoroammonium class. J. Chem. Soc. Perkin Trans. I, 1996, 2069.

* cited by examiner

Primary Examiner—Mukund J. Shah
Assistant Examiner—Venkataraman Balasubramanian
(74) Attorney, Agent, or Firm—Michael Leach

(57) ABSTRACT

Aromatic compounds having one or more electron-withdrawing substituents are fluorinated, preferably in a nitromethane solvent, by contact with tri(halo- or trifluoromethyl) substituted N-fluorotriazinium salts of the following Formula I:

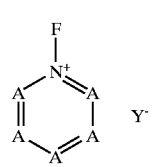

wherein three A moieties are independently CR, where each R is independently halogen or trifluoromethyl; two A moieties are independently Z, where each Z is independently nitrogen or a quaternary nitrogen atom and Y is a counterion or group of counterions which are inert to chemical attack by fluorine. Preferably the cation of the salt is 2,4,6-trichloro-1,3,5-triazinium.

22 Claims, No Drawings

US 6,635,760 B2

RING FLUORINATION OF NON-ACTIVATED AROMATIC COMPOUNDS

CROSS REFERENCES TO RELATED APPLICATIONS

Not applicable

STATEMENT REGARDING FEDERALLY SPONSORED RESEARCH OR DEVELOPMENT

Not applicable

BACKGROUND OF THE INVENTION

This invention relates to the use of tri(halo- or trifluoromethyl) substituted N-fluorotriazinium salts to fluorinate non-activated aromatic compounds (i.e. unsubstituted aromatic compounds and aromatic compounds having one or more electron-withdrawing substituents).

Fluorination is an important process in many areas of industry, in particular where the synthesis of specialty chemicals is concerned. Known fluorination methods are conveniently categorized according to the perceived manner in which the fluorinating agents provide fluorine for combination with an active site in an organic molecule, namely as fluorine atom (F˙), fluoride ion (F$^-$) or, conceptually, fluoronium ion (F$^+$). Fluorinations involving fluorine atom are notoriously exothermic and non-selective, hence "light" strategic fluorination of organic compounds (that is, the introduction of one or two fluorine substituents or a trifluoromethyl group at key molecular sites) rests on the availability of versatile ranges of nucleophilic and electrophilic sources of fluorine. Of late, the use of N-fluoro compounds has become one of the most widely used methods for the selective formation of carbon-fluorine bonds via "electrophilic" mechanisms. A recent comprehensive review of this synthetic methodology contains no reference to N-F reagents derived from triazines (see G. G. Furin in Methods of Organic Chemistry (Houben-Weyl): Volume E10a; Organofluorine Compounds (ed. B. Baasner, H. Hagemann, and J. C. Tatlow), Georg Thieme Verlag, Stuttgart, 1999, pp. 432–499.

1-Chloromethyl-4-fluoro-1,4-diazoniabicyclo[2.2.2] octane bis(tetrafluoroborate) (so-called F-TEDA-BF$_4$) is a known, commercially available (under the trade name "Selectfluor") fluorinating agent and is useful as a general purpose fluorinating agent. However this material has only a moderate fluorinating power and is able to fluorinate benzene only under forcing conditions, for example under reflux for 24 hours. The chemistry of F-TEDA-BF$_4$ has been reviewed by R. E. Banks in J. Fluorine Chemistry 87 (1998) 1–17, the whole content of which is incorporated herein by reference.

N-Fluoropyridinium salts and ring-substituted analogues thereof, e.g. N-fluoropyridinium triflate, are known for use as a fluorinating agent but have relatively low fluorinating power. U.S. Pat. No. 4,828,764 discloses that certain N-fluoro-N-perfluoroalkyl or perfluoroaryl sulfonamides including, inter alia, those of the formula R$_f$SO$_2$NFR are electrophilic fluorinating agents. In this formula R$_f$ represents a perfluorinated C$_1$–C$_{30}$ alkyl, C$_3$–C$_{30}$ cycloalkyl, C$_6$–C$_{14}$ aryl substituted C$_1$–C$_{10}$ alkyl or a C$_6$–C$_{14}$ aryl group and R represents a C$_1$–C$_{30}$ alkyl, C$_3$–C$_{30}$ cycloalkyl, C$_6$–C$_{14}$ aryl substituted C$_1$–C$_{10}$ alkyl, or C$_6$–C$_{14}$ aryl group optionally substituted with one or more inert substituents including, inter alia, fluorine and, when R$_f$ is trifluoromethyl, R alternatively can represent perfluoromethyl-sulfonamido.

The preferred fluorinating agents are stated to be N-fluorobis-(trifluoromethanesulfonyl)imide (R$_f$=CF$_3$ and R=CF$_3$SO$_2$), known as DesMarteau's Reagent, and N-fluoro-N-methyltrifluoromethanesulfonamide (R$_f$=CF$_3$ and R=CH$_3$). DesMarteau's Reagent is a powerful electrophilic fluorinating agent which is capable of converting benzene to fluorobenzene at room temperature but is hazardous, time-consuming and expensive to prepare requiring eight or nine reaction steps from readily available material. Only a very limited number of other known fluorinating agents are strong enough to fluorinate benzene without forcing conditions but they often provide relatively low yields or require special precautions. Those reported to fluorinate benzene include, in addition to DesMarteau's Reagent, CF$_3$OF, XeF$_2$, NF$_4^+$, BF$_4^-$, N$_2$F$^+$AsF$_6^-$, N-fluoropentachloropyridium triflate, perfluoro-[N-fluoro-N-(4-pyridyl)methanesulfonamide] and N-fluoro-2,6-bis (methoxycarbonyl)pyridinium triflate. Very few of these compounds, only NF$_4^+$ BF$_4^-$ and XeF$_2$, are known to fluorinate aromatic substrates having electron-withdrawing substituents such as nitrobenzene.

N-Fluorotriazinium salts of the following Formula A are known:

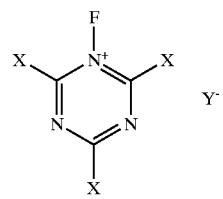

(A)

wherein:
(i) X=H & Y$^-$=AsF$_6^-$ (Ref.1—see below)
(ii) X=F & Y$^-$=AsF$_6^-$ (Ref. 2—see below)
(iii) X=F & Y$^-$=BF$_4^-$ (Ref. 3—see below) and
(iv) X=Cl & Y$^-$=AsF$_6^-$ (Refs. 2 & 4—see below).

The N-fluorotriazinium salts of Formula A are reported to be oxidizing agents of use in, for example, organometallic chemistry. The cationic component of compounds of Formula A in which X is H, F and Cl have been described as "oxidative fluorinators" and a qualitative scale for their oxidizing strength and that of NF$_4^+$ has been computed ab initio (Ref. 3—see below).

Ref. 1=Broschag et al. Inorg. Chim. Acta, 205 (1993) 167–173;
Ref. 2=Schleyer et al. Inorg. Chem. 32 (1993) 1523–1524;
Ref. 3=Schulz and Klapötke J. Organometal. Chem. 480 (1994) 195–197; and
Ref. 4=Broschag et al. Z. Anorg. Allg. Chem., 620 (1994) 1132–1136.

There is a statement in Schleyer et al. that 1-fluoro-2,4, 6-trichloro-s-triazinium hexafluoroarsenate (Formula A; X=Cl; and Y$^-$=AsF$_6^-$) "is a promising fluorination agent" but no further details were provided or subsequently reported. It is believed that uses of the compounds of Formula A other than as oxidizing agents was not contemplated or investigated. In particular, there is no disclosure in the prior art of any of these compounds being evaluated as oxidative fluorinators (as distinct from non-fluorinating oxidizing agents) despite the computed values reported in Refs. 3 and 4.

BRIEF SUMMARY OF THE INVENTION

We have now surprisingly found that tri(halo- or trifluoromethyl) substituted N-fluorinated triazinium salts are sufficiently strong electrophilic fluorinating agents that they will readily fluorinate non-activated aromatic compounds. The N-fluorotriazinium salts can be represented by the following Formula I:

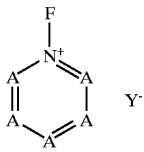
(I)

in which:

three A moieties are independently CR, where each R is independently halogen or trifluoromethyl;

two A moieties are independently Z, where each Z is independently nitrogen or a quaternary nitrogen atom; and Y⁻ is a counterion or group of counterions which are inert to chemical attack by fluorine.

DETAILED DESCRIPTION OF THE INVENTION

In its broadest aspect, the present invention provides a method of fluorinating a substrate selected from the group consisting of unsubstituted aromatic compounds and aromatic compounds having one or more electron-withdrawing substituents which comprises contacting the substrate with a tri(halo- or trifluoromethyl) substituted N-fluorotriazinium salt.

The N-fluorotriazinium salts are of the following Formula I:

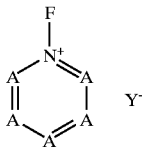
(I)

wherein:

three A moieties are independently CR, where each R is independently halogen or trifluoromethyl;

two A moieties are independently Z, where each Z is independently nitrogen or a quaternary nitrogen atom; and Y⁻ is a counterion or group of counterions which are inert to chemical attack by fluorine.

It is presently preferred that the triazinium compounds are 1,2,4-triazinium compounds of the following Formula IA or, especially, 1,3,5-triazinium compounds of the following Formula IB:

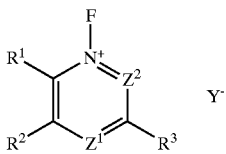
(IA)

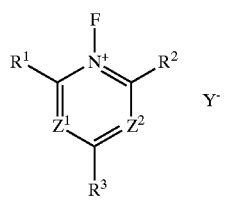
(IB)

wherein:

R¹, R² and R³ are independently halogen or trifluoromethyl;

Z¹ and Z² are independently nitrogen or a quaternary nitrogen atom; and

Y⁻ is a counterion or group of counterions which are inert to chemical attack by fluorine.

As mentioned above, the N-fluoro-triazinium salts of Formula I are remarkably strong fluorinating agents capable of room temperature fluorination of unsubstituted aromatic substrates such as benzene and aromatic substrates having one or more electron-withdrawing substituents such as chlorobenzene or nitrobenzene.

Usually, all R substituents, or R¹, R² and R³ for Formulae IA and IB, are identical in a given compound.

The compounds of Formula I contain at least one fluorinated quaternary nitrogen atom in the triazinium ring and one or both of the other triazinium nitrogen atoms may be quaternary, preferably fluorinated, nitrogen. In a preferred embodiment both Z, or both Z¹ and Z² for Formulae IA and IB, are nitrogen and the most preferred compounds are those of the following Formula II:

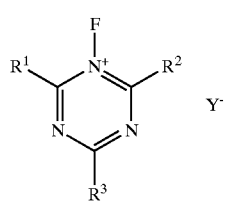
(II)

wherein R¹, R², R³ and Y⁻ are as defined above.

Examples of preferred compounds according to the invention are those having a triazinium cation as shown below in Formulae III to V.

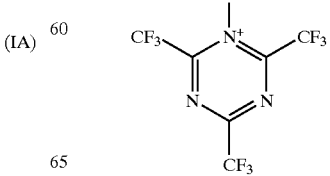
(III)

1-fluoro-2,4,6-tris(trifluoromethyl)-1,3,5-triazinium

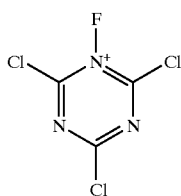

(IV)

1-fluoro-2,4,6-trichloro-1,3,5-triazinium

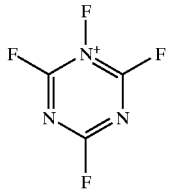

(V)

1-fluoro-2,4,6-trifluoro-1,3,5-triazinium

The counterion Y⁻ is resistant to chemical attack by fluorine and desirably, is thermally stable and possesses low environmental toxicity. The counterion(s) can be any anion (s) which can be counterion(s) to the triazinium cation. The counterion(s) may have a single charge or a multiple charge or be a group of counterions so as to balance the charge of the triazinium moiety. Also the counterion may be a counterion to more than one mole of the triazinium cation, for example where the cation has a single charge and the counterion has a multiple charge.

Suitably the counterion is weakly nucleophilic. Suitable anions include fluoride; fluorosulfate ($SO_3F^-$); alkanesulfonate, especially methanesulfonate ($CH_3SO_3^-$); alkyl sulfate, especially methyl sulfate ($CH_3SO_4^-$); perfluoroalkanesulfonate, preferably triflate ($CF_3SO_3^-$) and nonaflate ($C_4F_9O_3^-$); arenesulfonate, especially tosylate (i.e. p-toluenesulfonate; p-$CH_3C_6H_4SO_3^-$); alkanecarboxylate; perfluoroalkanecarboxylate; tetrafluoroborate ($BF_4^-$); tetraphenylborate ($Ph_4B^-$); hexafluorophosphate ($PF_6^-$); hexafluoroantimonate ($SbF_6^-$); hexafluoroarsenate ($AsF_6^-$); chlorate ($ClO_3^-$); sulfate ($SO_4^{2-}=2Y^-$); hydrogen sulfate ($HSO_4^-$) and $F(HF)_x^-$ where x is at least 1. Presently preferred counterions include fluoride, tetrafluoroborate, triflate, tosylate, hexafluoroarsenate and hexafluorophosphate.

Preferably, the compounds of Formula I are prepared using a solvent-based process which comprises contacting a triazine compound with a fluorine source under acidic conditions in a solvent which is inert under the process conditions.

Suitably the fluorine source is an electrophilic fluorine source such as, for example, fluorine gas or a mixture of fluorine gas and a neutral compound derivable from a fluorine-containing counterion Y⁻ by removing at least one fluoride ion from Y⁻, for example boron trifluoride. Preferably, the fluorine source is fluorine gas. While the fluorine gas may be used without dilution, in general, it is preferable to use fluorine gas diluted with an inert gas so that the volume of the inert gas is between about 99.9% and about 50% for controlling the vigorous reaction. Suitable inert gases include nitrogen, helium and argon.

The triazine compound to be fluorinated is suitably a compound of the Formula VI and may be obtained by subjecting a compound or a mixture of compounds of formula RCN to a known process for producing a triazine compound of formula (RCN)₃, wherein R is independently $R^1$, $R^2$ or $R^3$ as described herein:

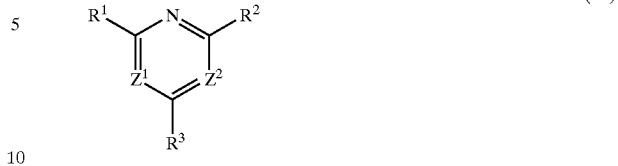

(VI)

The fluorination process is carried out in the presence of an acid which may be a Brønsted acid (organic or mineral) or a Lewis acid. The level of acid is suitably adjusted so as to reduce and desirably avoid double protonation of the triazine compound and to provide a yield (as determined by ¹⁹F NMR) of F—N⁺ of at least about 20% and desirably of at least about 50%. Desirably the molar ratio of acid to triazine substrate is about 0.5 to about 2.5, preferably about 1 to about 2.2.

Preferable examples of Brønsted acid have pKa in the range from about 12.4 to about 4.6 and include halogenated alcohols, for example chlorodifluoroethanol, dichlorofluoroethanol, chlorooctafluoro-t-butanol, trifluoroethanol, tetrafluoropropanol, pentafluoropropanol, hexafluoroisopropanol, octafluoropentanol, and nonafluoro-t-butanol. Fluorinated alcohols, particularly those which are free of chlorine, are especially preferred.

Other acids which are especially preferred include acids of the counterion Y⁻ described above, for example anhydrous hydrofluoric acid, hexafluoroantimonic acid, tetrafluoroboric acid and triflic acid, sulfuric acid, methanesulfonic acid, acetic acid and trifluoroacetic acid.

Brønsted acids may be used in the form of a complex with ethers, water, alcohols, nitriles, carboxylic acids and the like and may be used in the form of an aqueous solution.

Preferably, the solvent is non-aqueous and it is presently particularly preferred that the solvent is acetonitrile, a halogenated, especially fluorinated, alcohol or, especially, nitromethane. In this connection, it is believed that there has not been any previous proposal to use nitromethane as a solvent, or for any other purpose, with any N-F or ⁺N-F reagent.

If desired the same material may be used as both the acid and the solvent.

The reaction to produce a compound of Formula I is carried out at a temperature at which the solvent is in the liquid phase and suitably at a sufficiently low temperature that reaction due to a free radical mechanism is reduced and suitably avoided. The particular temperature selected depends on the solvent and also the reactants. By way of example only, the reaction suitably may be carried out at a temperature of about −40 to about 10° C. A temperature of about −40 to about −20° C. is preferred for acetonitrile and a temperature of about −10 to about 5° C. is preferred for hexafluoroisopropyl alcohol. The reaction may be carried out at elevated pressure although this is not essential.

Fluorination of the triazine compound may be carried out using a stirred-tank batch reactor. Where the fluorine source is gaseous, the fluorine source is suitably admitted either as neat gas at sub-atmospheric pressure or as a continuous flow of fluorine blended with nitrogen or other inert diluent at about atmospheric pressure. Advantageously, the process for producing compound of Formula I may be operated as a continuous process.

The compounds of Formula I may be used as electrophilic fluorinating agents in a similar manner to Selecfluor™ and in manner know in the art (see, for example, R. E. Banks et al. J. Chem. Soc. Perkin Trans. I, 1996, 2069). The fluorinating agent may be contacted with the substrate neat and optionally at elevated temperature. If desired the fluorination process may be carried out in a solvent, for example acetonitrile or, especially, nitromethane. As mentioned above, it is believed that there has not been any previous proposal to use nitromethane as a solvent, or for any other purpose, with any N-F or $^+$N-F reagent.

When a compound of Formula I has been used in a fluorination reaction and so depleted in fluorine, it may be recovered and regenerated by introducing the fluorine source for reuse in further fluorination reactions.

Compounds of Formula I may be isolated or used without separation from the reaction mixture. If desired, the reaction mixture may be fed to a separate fluorination reactor or the compound of Formula I may be purified or otherwise treated prior to use.

Accordingly, the invention also provides a method of producing a fluorinated substrate which comprises contacting, preferably under acidic conditions, a tri(halo or trifluoromethyl)triazine compound with a fluorine source in a solvent, which is inert under the process conditions, such that at least one of the nitrogen atoms in the triazine compound is fluorinated to produce a compound of Formula I and contacting, in situ or subsequently, the compound with a substrate to be fluorinated.

The invention is illustrated by the following non-limiting Examples.

EXAMPLE 1

Preparation of 1-fluoro-2,4,6-trichloro-1,3,5-triazinium triflate

Cyanuric chloride (0.1 g, 0.54 mmol), triflic acid (0.08 g, 0.53 mmol) and acetonitrile (80 cm$^3$) were placed in the flow fluorination reactor, cooled to −35° C., stirred vigorously and treated with a 1:9 (v/v) fluorine-nitrogen blend (flow rate of 130 cm$^3$ per minute) until the exit gas gave a strong positive test (KI) for fluorine. A small sample (20 cm$^3$) of the resulting colorless reaction solution was tested for oxidation properties with aqueous KI and gave a strong positive result. A sample (20 cm$^3$) of the cold (−35° C.) reaction solution was treated with dry benzene (2.0 cm$^3$) and the homogeneous mixture left to warm to room temperature before being analyzed by $^{19}$F NMR, using D$_2$O as an external lock. The spectrum showed the characteristic absorption for fluorobenzene at $\delta_F$ −36.2 (m) ppm (TFA (trifluoroacetic acid) ref.). The remaining reaction solution was evaporated under reduced pressure, yielding a white solid which fumed in air. The $^{19}$F NMR spectrum of this fuming solid (dissolved in CD$_3$CN) was found to contain the expected OTf$^-$ absorption at 5.4(s) ppm (TFA ref.), as well as an absorption at 39.3 (br. s) ppm assignable to the $^+$NF function of 1-fluoro-2,4,6-trichloro-1,3,5-triazinium triflate. Owing to the highly hygroscopic nature of this white solid, a satisfactory elemental analysis was impossible to obtain; iodometric titration of a sample of this product revealed that the F$^+$ content was 62% (i.e. the percentage of oxidizing F$^+$ present per mole of the reagent). The reaction was repeated using hexafluoroisopropanol as the fluorination solvent, but the material obtained was only 86% pure (estimated by $^{19}$F NMR).

EXAMPLE 2

Fluorinations using 1-fluoro-2,4,6-trichloro-1,3,5-triazinium tetrafluoroborate in CD$_3$CN The required amount of 1-fluoro-2,4,6-trichloro-1,3,5-triazinium tetrafluoroborate was weighed into a glass vial in an efficient dry box (argon atmosphere) before it was added to a cold solution (0° C.) of the substrate in CD$_3$CN. The reaction mixture was allowed to warm to room temperature, transferred to a standard NMR tube and its spectrum measured.

1) Reaction with methoxybenzene

The reaction was carried out on both a 1:1 and 2:1 molar ratio basis (methoxybenzene: $^+$NF). In both experiments the reaction was immediate and exothermic, and the solution's changed color from yellow (at 0° C.) to dark violet at room temperature). After 8 hours, the $^{19}$F NMR spectra (188.8 MHz; 27° C.; CFCl$_3$) of the reaction solutions showed absorptions at $\delta_F$ (1:1 reaction) −126.6 (m, 4-F) and −137.8 (m, 2-F) and (1:2 reaction) −126.6 (m, 4-F) and −137.9 (m, 2-F) ppm (product ratio: 4-F:2-F, 2:1); other (unidentified) absorptions were observed at $\delta_F$ −123.2, −123.3, −132.0, and −132.9 ppm.

2) Reaction with benzene

The reaction was carried out using a 1:1 molar ratio of reactants. A progressive color change of the reaction solution was observed [colorless (0° C. to room temperature, 1.0 hour), pale yellow (room temperature, 2.0 to 4.0 hours), yellow to pale brown (room temperature, 4.0 to 8.0 hrs)], and after 8.0 hours the $^{19}$F NMR (CFCl$_3$) spectrum was measured and found to contain only the characteristic absorption for fluorobenzene at $\delta_F$ −115.2 (m) ppm and a BF$_4^-$ peak.

3) Reaction with chlorobenzene

The reaction was carried out on a 1:1 molar ratio basis. After 8.0 hours (room temperature; change from colorless to pale brown solution) the $^{19}$F NMR (CFCl$_3$) spectrum was measured and showed an absorption at $\delta_F$ −116.0 (m, 4-F) ppm assignable to 4-chlorofluorobenzene.

4) Reaction with nitrobenzene

The reaction was carried out on a 1:1 molar ratio basis. After 8.0 hours (room temperature; colorless solution changed to pale brown), the $^{19}$F NMR (CFCl$_3$) spectrum of the product was measured and showed an absorption at $\delta_F$ −109.4 (m, 3-F) which was more intense than an absorption associated with decomposition of 1-fluoro-2,4,6-trichloro-1,3,5-triazinium tetrafluoroborate (see below) and hence indicated that 3-fluoronitrobenzene had been formed.

5) $^{19}$F NMR examination of 1-fluoro-2,4,6-trichloro-1,3,5-triazinium tetrafluoroborate in CD$_3$CN A solution of 1-fluoro-2,4,6-trichloro-1,3,5-triazinium tetrafluoroborate in CD$_3$CN was made at room temperature (colorless) and its $^{19}$F NMR (ref. CFCl$_3$) spectrum was measured immediately; this showed absorptions at +15.3 (br.s., $^+$NF) ppm and −146.7 (br.s., BF$_4^-$) ppm. A number of minor peaks were observed in the region between $\delta_F$ −1.0 and −110 ppm, suggesting that a decomposition of the $^+$NF salt was taking place. The sample was left standing for 2.0 hours (the solution's color changed to pale yellow) before the spectrum was measured again; this revealed that the intensity of $^+$NF absorption at $\delta_F$ +15.3 had markedly decreased, while the intensities of the absorption peaks associated with decomposition of the salt ($\delta_F$ −1.0 to −110 ppm) had noticeably increased. These minor absorptions were present in the spectra of all of the products from the above reactions.

EXAMPLE 3

Fluorinations using 1-fluoro-2,4,6-trichloro-1,3,5-triazinium tetrafluoroborate Without Solvent A suspension of 1-fluoro-2,4,6-trichloro-1,3,5-triazinium tetrafluoroborate (0.1 g, 3.4 mmol) and an excess of the substrate was prepared in a sealed tube at room temperature (using an argon-filled dry box). The mixture was heated to about 60° C. for a few minutes, then cooled to room temperature, before a small sample was syringed out and filtered to remove any insoluble materials (i.e. 1-fluoro-2,4,6-trichloro-1,3,5-triazinium tetrafluoroborate) before its $^{19}$F NMR (CFCl$_3$) spectrum was measured using D$_2$O as an external lock.

1) Reaction with benzene

The $^{19}$F NMR spectrum of the product was measured immediately and showed the characteristic absorptions for monofluorobenzene at $\delta_F$ −113.3(m) ppm and 1,4-difluorobenzene at $\delta_F$ −119.9 ppm, with a ratio of approximately 2:1. A KI test of the reaction mixture gave a strong positive result, indicating that the reaction had not gone to completion at this stage, and the reaction mixture was left standing at room temperature for 14 days (an excessive period, negative KI test at this stage). The $^{19}$F NMR spectrum of the sample was then measured again and revealed the presence of another difluoro-isomer, namely 1,2-difluorobenzene [$\delta_F$ −138.7 (m) ppm; the ratio of 1,4- to 1,2-$C_6H_4F_2$ was about 2:1].

2) Reaction with chlorobenzene

The 19F NMR spectrum of the product was measured shortly after the reaction had been carried out and found to contain absorptions at $\delta_F$ −111.0 (m, 3-F); −115.7 (m, 2-F) and −116.1 (m, 4-F) (the ratio of 2-:3-:4-isomers was about 1:0.3:2). After 14 days (negative KI test), the $^{19}$F NMR spectrum showed no evidence for the presence of any other products.

3) Reaction with nitrobenzene

The $^{19}$F NMR spectrum of the reaction solution contained one weak absorption assignable to 3-fluoronitrobenzene at $\delta_F$ −110.27 (m) after about 25 minutes. After 14 days (positive KI test still) however, the $^{19}$F NMR spectrum showed absorptions corresponding to 3-fluoronitrobenzene at $\delta_F$ −110.3 (m) and 2-fluoronitrobenzene at $\delta_F$ −119.1 (m) (ratio about 2:1); also, in keeping with the result of the KI test, the $^+$NF absorption of the reagent was still present.

A homogeneous reaction mixture was obtained in this experiment, whereas in the aforementioned fluorinations of benzene and chlorobenzene, the reaction mixtures contained suspended [(ClCN)$_3$F]$^+$BF$_4^-$. In order to drive the fluorination of nitrobenzene to completion, the reaction mixture was heated at 90° C. for 2 hours before it was tested with KI solution and gave a negative result. G.C. analysis revealed the presence of only 3-fluoronitrobenzene and 2-fluoronitrobenzene with no marked change in ratio (about 2:1 ratio). Despite the presence of the 2-fluoro derivative, no evidence were obtained for the presence of 4-fluoronitrobenzene. The absence of 4-fluoronitrobenzene may have resulted from loss of this isomer during the reaction or subsequent handling operations via nucleophilic displacement of the highly mobile fluorine. In this connection, the reaction vessel became etched during the reaction.

EXAMPLE 4

(i) Preparation of 1-fluoro-2,4.6-tris(trifluoromethyl)-1,3,5-triazinium triflate 2,4,6-Tris(trifluoromethyl)-1,3,5-triazine (0.2 g, 0.7 mmol), triflic acid (0.11 g, 0.73 mmol) and hexafluoroisopropanol (80 cm$^3$) were placed in a flow fluorination reactor, cooled (−5° C.), stirred vigorously and treated with a 1:9 (vol./vol.) fluorine-nitrogen blend (flow rate of 130 cm$^3$ per minute) until the exit gas gave a strong positive test (KI) for fluorine. A small sample (10 cm$^3$) of the resultant colorless reaction solution was tested for oxidation properties with aqueous KI and gave a strong positive test. The remaining reaction solution was evaporated under reduced pressure, yielding a colorless oily material, which fumed when exposed to air. The $^{19}$F NMR spectrum of this material (in CD$_3$CN) contained the expected OTf$^-$ and CF$_3$ at $\delta_F$+0.5-6.0 (s; TFA ref.) ppm as well as a weak absorption at +28.3 (br. s) assignable to the $^+$NF function of 1-fluoro-2,4,6-tris (trifluoromethyl)-1,3,5-triazinium triflate. The reaction was repeated a number of times, but no pure $^+$NF salt was isolated, believed to be due to the hygroscopic nature of $^+$NF salt and its reactivity towards water.

(ii) Fluorination of benzene with 1-fluoro-2,4.6-tris (trifluoromethyl)-1,3,5-triazinium triflate A sample (30 cm$^3$) of the cold (−5° C.) reaction solution from (i) above was treated with dry benzene (2.0 cm$^3$) and the homogeneous mixture left to warm to room temperature overnight before being analyzed by $^{19}$F NMR, using D$_2$O as an external lock. The spectrum showed the characteristic absorption for fluorobenzene at $\delta_F$ −364 (m; TFA ref.) ppm.

EXAMPLE 5

Fluorinations using 1-fluoro-2,4,6-trichloro-1,3,5-triazinium tetrafluoroborate in nitromethane A solution of 1-fluoro-2,4,6-trichloro-1,3,5-triazinium tetrafluoroborate (0.1 g, 3.4 mmol) and the substrate in equimolar proportion was prepared in nitromethane (20 cm$^3$) in a sealed tube at room temperature (except for the reaction involving methoxybenzene), using an argon-filled dry box. Reaction progress was determined by removing small samples via a syringe and subjecting them to $^{19}$F NMR analysis (CFCl$_3$ ref.; D$_2$O ext. lock).

1) Reaction with methoxybenzene

The reaction was carried out on both a 1:1 and 2:1 molar ratio basis (methoxybenzene:$^+$NF). In both experiments the reaction was immediate and exothermic, and the solutions changed color from colorless (at about −20° C.) to dark violet (at room temperature). After 2.0 hours (-ve KI test), the $^{19}$F NMR spectra (188.8 MHz; 27° C., CFCl$_3$) of the reaction solutions showed absorptions at $\delta_F$ (1:1 reaction) −126.6 (m, 4-F) and −137.8 (m, 2-F), and (1:2 reaction) −126.6 (m, 4-F) and −137.9 (m, 2-F) ppm (product ratio: 4-F:2-F =2:1).

2) Reaction with benzene

The $^{19}$F NMR spectrum of the product was measured immediately and showed the characteristic absorptions for monofluorobenzene at $\delta_F$ −113.3 (m) ppm and 1,4-difluorobenzene at $\delta_F$ −119.9 ppm, with a ratio of approximately 2:1. A KI test on the reaction mixture gave a strong positive result, indicating that the reaction had not gone to completion at this stage, hence, the reaction mixture was heated to 70° C. and its $^{19}$F NMR spectrum measured at intervals to determine the progress of reaction. After 2.0 hours, the spectrum showed only absorptions for fluorobenzene and 1,4-difluorobenzene and the reaction mixture still gave a positive KI test. However, after 6.0 hours a negative KI test was obtained, indicating that consumption of the NF reagent was complete, and $^{19}$F NMR analysis revealed the presence of another difluorinated isomer, namely 1,2-difluorobenzene [$\delta_F$ −138.7 (m) ppm; the ratio of 1,4- to 1,2-$C_6H_4F_2$ was about 2:1].

3) Reaction with chlorobenzene

The $^{19}$F NMR spectrum of the reaction solution was measured shortly after it had been prepared and found to contain absorptions at $\delta_F$ −111.0 (m, 3-F); −115.7 (m, 2-F) and −116.1 (m, 4-F) (the ratio of 2-: 3-: 4-isomers was about 1:0.3:2). After heating the solution at 70° C. for 6.0 hours (negative KI test), its $^{19}$F NMR spectrum showed no evidence for the presence of any other products.

4) Reaction with nitrobenzene

The $^{19}$F NMR spectrum of the reaction solution contained one weak absorption assignable to 3-fluoronitrobenzene at $\delta_F$ −110.27 (m) after about 25 minutes. After 6.0 hours of heating at 70° C. (positive KI test still) however, the $^{19}$F NMR spectrum showed absorptions corresponding to 3-fluoronitrobenzene at $\delta_F$ −110.3 (m) and 2-fluoronitrobenzene at $\delta_F$ −119.1 (m) (ratio about 2:1);

also, in keeping with the result of a KI test (weakly positive), the $^+$NF absorption of the reagent was still present.

EXAMPLE 6

Preparation of 1-fluoro-2,4,6-trichloro-1,3,5-triazinium triflate in nitromethane Cyanuric chloride (0.1 g, 0.54 mmol), triflic acid (0.08 g, 0.53 mmol) and nitromethane (80 cm$^3$) were placed in a flow fluorination reactor, cooled (about −30° C.), stirred vigorously and treated with a 1:9 (v/v) fluorine-nitrogen blend (flow-rate 130 cm$^3$ per minute) until the exit gas gave a strong positive test (KI) for fluorine. A small sample (20 cm$^3$) of the resulting colorless reaction solution was tested for oxidation properties with aqueous KI and gave a strong positive result. A sample (20 cm$^3$) of the cold (about −30° C.) reaction solution was treated with dry benzene (2.0 cm$^3$) and the homogeneous mixture left to warm to room temperature before being analyzed by $^{19}$F NMR, using D$_2$O as an external lock. The spectrum showed the characteristic absorption for fluorobenzene at $\delta_F$ −36.2 (m) ppm (TFA ref.). The remaining reaction solution was allowed to warm to room temperature (it remained clear and colorless) then evaporated under reduced pressure, yielding an off-white solid which fumed profusely in air. The $^{19}$F NMR spectrum of this fuming solid (dissolved in CH$_3$NO$_2$ and using D$_2$O as an external lock) was found to contain the expected OTf$^-$ absorption at 5.4 (s) ppm (TFA ref.), as well as an absorption at 39.3 (br. s) ppm assignable to the $^+$NF function of 1-fluoro-2,4,6-trichloro-1,3,5-triazinium triflate. Owing to the highly hygroscopic nature of this white solid, no further analysis was obtained.

The above reaction was repeated using CH$_3$NO$_2$ diluted with CHCl$_3$ (mixtures containing 10%, 50% and 80% of CH$_3$NO$_2$ were studied) as a solvent. Fluorination proceeded more cleanly as the proportion of nitromethane increased; thus, while use of neat CH$_3$NO$_2$ or 80% CH$_3$NO$_2$ produced clean, colorless reaction solutions at room temperature, use of the lower concentrations of CH$_3$NO$_2$ gave colored solutions (dark brown at 10% concentration; pale yellow at 50%), again after the reaction solutions had warmed to ambient temperature.

It will be appreciated that the invention is not restricted to the details described above with reference to the preferred embodiments but that numerous modifications and variations can be made without departing from the scope or spirit of the invention.

We claim:

1. A method of fluorinating a substrate selected from the group consisting of aromatic compounds having one or more electron-withdrawing substituents which comprises contacting the substrate with a tri(halo- or trifluoromethyl) substituted N-fluorotriazinium salt of the following Formula I:

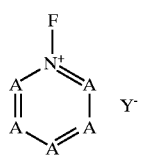

(I)

wherein
three A moieties are independently CR, where each R is independently halogen or trifluoromethyl;
two A moietios are independently Z, where each Z is independently nitrogen or a quaternary nitrogen atom; and
Y$^-$ is a counterion or group of counterions which are inert to chemical attack by fluorine.

2. The method according to claim 1, wherein the N-fluorotriazinium salt is a N-fluoro-1,2,4-triazinium compound of the following Formula IA:

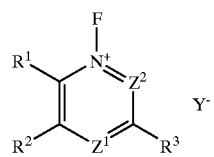

(IA)

wherein:
R$^1$, R$^2$ and R$^3$ are independently halogen or trifluoromethyl;
Z$^1$ and Z$^2$ are independently nitrogen or a quaternary nitrogen atom and
Y$^-$ is a counterion or group of counterions which are inert to chemical attack by fluorine.

3. The method according to claim 1, wherein the N-fluorotriazinium salt is a N-fluoro-1,3,5-triazinium compound of the following Formula IB;

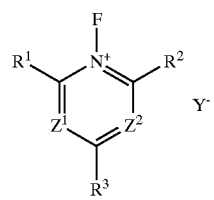

(IB)

wherein
R$^1$, R$^2$ and R$^3$ are independently halogen or trifluoromethyl;
Z$^1$ and Z$^2$ are independently nitrogen or a quaternary nitrogen atom and
Y$^-$ is a counterion or group of counterions which are inert to chemical attack by fluorine.

4. The method according to claim 1, wherein the R substituents are selected from the group consisting of chlorine, fluorine and trifluoromethyl.

5. The method according to claim 4, wherein the aromatic substrate is selected from the group consisting of chlorobenzene and nitrobenzene.

6. The method according to claim 1, wherein the R substituents are identical.

7. The method according to claim 6, wherein each R is chlorine.

8. The method according to claim 6, wherein each R is fluorine.

9. A method of fluorinating a substrate selected from the group consisting of unsubstituted aromatic compounds and aromatic compounds having one or more electron-withdrawing substituents which comprises contacting the substrate with a tri(halo- or trifluoromethyl) substituted N-fluorotriazinium salt of the following Formula I:

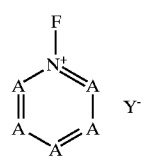

(I)

wherein:

three A moieties are independently CR, where each R is independently halogen or trifluoromethyl;

two A moieties are independently Z, where each Z is independently nitrogen or a quaternary nitrogen atom; and Y⁻ is a counterion or group of counterions which are inert to chemical attack by fluorine;

wherein each R is trifluoromethyl.

10. The method according to claim 1, wherein both Z are nitrogen or fluorinated quaternary nitrogen.

11. The method according to claim 10, wherein both Z are nitrogen.

12. The method according to claim 11, wherein the N-fluorotriazinium salt is a N-fluoro-1,3,5-triazinium compound of the following Formula II:

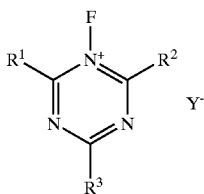

(II)

wherein R¹, R², R³ and Y⁻ are as defined in claim 1.

13. The method according to claim 12, wherein the N-fluorotriazinium salt is a N-fluoro-2,4,6-trichloro-1,3,5-triazinium compound of the following Formula IIA:

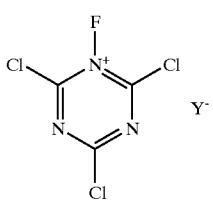

(IIA)

wherein Y⁻ is a counterion or group of counterions which are inert to chemical attack by fluorine.

14. The method according to claim 12, wherein the N-fluorotriazinium salt is a N-fluoro-2,4,6-trifluoro-1,3,5-triazinium compound of the following Formula IIB:

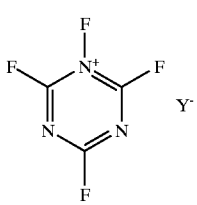

(IIB)

wherein Y⁻ is a counterion or group of counterions which are inert to chemical attack by fluorine.

15. A method or fluorinating a substrate selected from the group consisting of unsubstituted aromatic compounds and aromatic compounds having one or more electron-withdrawing substituents which comprises contacting the substrate with a N-fluoro-2,4,6-tris(trifluoromethyl)-1,3,5-triazinium compound of the following Formula IIC:

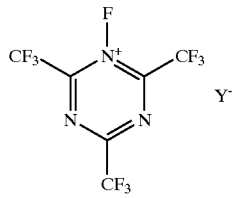

(IIC)

wherein Y⁻ is a counterion or group of counterions which are inert to chemical attack by fluorine.

16. The method according to claim 1, wherein Y⁻ is selected from the group consisting of fluoride, fluorosulfate, alkanesulfonate, alkyl sulfate, perfluoroalkanesulfonate, arenesulfonate, alkanecarboxylate, perfluoroalkanecarboxylate, tetrafluoroborate, tetraphenylborate, hexafluorophosphate, hexafluoroantimonate, hexafluoroarsenate, chlorate, sulfate (=2Y⁻), hydrogen sulfate and $F(HF)_x^-$ where x is at least 1.

17. The method according to claim 16, wherein Y⁻ is selected from the group consisting of fluoride, tetrafluoroborate, triflate, tosylate, hexafluoroarsenate and hexafluorophosphate.

18. The method according to claim 17, wherein Y⁻ is triflate.

19. The process according to claim 1, wherein the contacting is performed in a solvent comprising nitromethane.

20. A method of fluorinating a substrate selected from the group consisting of aromatic compounds having one or more electron-withdrawing substituents which comprises contacting the substrate with a N-fluoro-1,3,5-triazinium compound of the following Formula II:

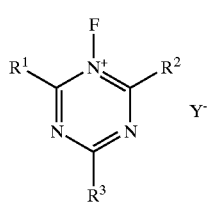

(II)

wherein:

R¹, R², and R³ are selected from the group consisting of chlorine, fluorine and trifluoromethyl and Y⁻ is selected from the group consisting of fluoride, fluorosulfate, alkanesulfonate, alkyl sulfate, perfluoroalkanesulfonate, arenesulfonate, alkanecarboxylate, perfluoroalkanecarboxylate, tetrafluoroborate, tetraphenylborate, hexafluorophosphate, hexafluoroantimonate, hexafluoroarsenate, chlorate, sulfate (=2Y⁻), hydrogen sulfate and $F(HF)_x^-$ where x is at least 1.

21. The method according to claim 20, wherein Y⁻ is selected from the group consisting of fluoride, tetrafluoroborate, triflate, tosylate, hexafluoroarsenate and hexafluorophosphate.

22. The method according to claim 21, wherein each of R¹, R², and R³ is identical.

* * * * *

UNITED STATES PATENT AND TRADEMARK OFFICE
CERTIFICATE OF CORRECTION

PATENT NO. : 6,635,760 B2 Page 1 of 1
DATED : October 21, 2003
INVENTOR(S) : Ronald Eric Banks et al.

It is certified that error appears in the above-identified patent and that said Letters Patent is hereby corrected as shown below:

<u>Column 14,</u>
Line 30, after "consisting of," insert -- unsubstituted aromatic compounds and --

Signed and Sealed this

Seventeenth Day of February, 2004

JON W. DUDAS
*Acting Director of the United States Patent and Trademark Office*